US00PP31151P2

(12) United States Plant Patent
Robb

(10) Patent No.: US PP31,151 P2
(45) Date of Patent: Dec. 3, 2019

(54) ***GARDENIA* PLANT NAMED 'PARWHI'**

(50) Latin Name: *Gardenia augusta*
Varietal Denomination: PARWHI

(71) Applicant: John Robb, Kulnura (AU)

(72) Inventor: John Robb, Kulnura (AU)

(73) Assignee: Paradise Seed Company Pty Ltd (AU)

( * ) Notice: Subject to any disclaimer, the term of this patent is extended or adjusted under 35 U.S.C. 154(b) by 0 days.

(21) Appl. No.: 15/999,946

(22) Filed: Aug. 30, 2018

(51) Int. Cl.
*A01H 5/02* (2018.01)
*A01H 6/76* (2018.01)

(52) U.S. Cl.
USPC ..... Plt./255

(58) Field of Classification Search
USPC ..... Plt./226, 255
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Gardenia* cultivar named 'PARWHI' is disclosed, characterized by distinctive compact, semi-erect plant habit. Flowers produced by the new variety have numerous petals, forming a semi-double flower. The new cultivar is a *Gardenia*, suitable for ornamental garden purposes.

2 Drawing Sheets

Figure 1:
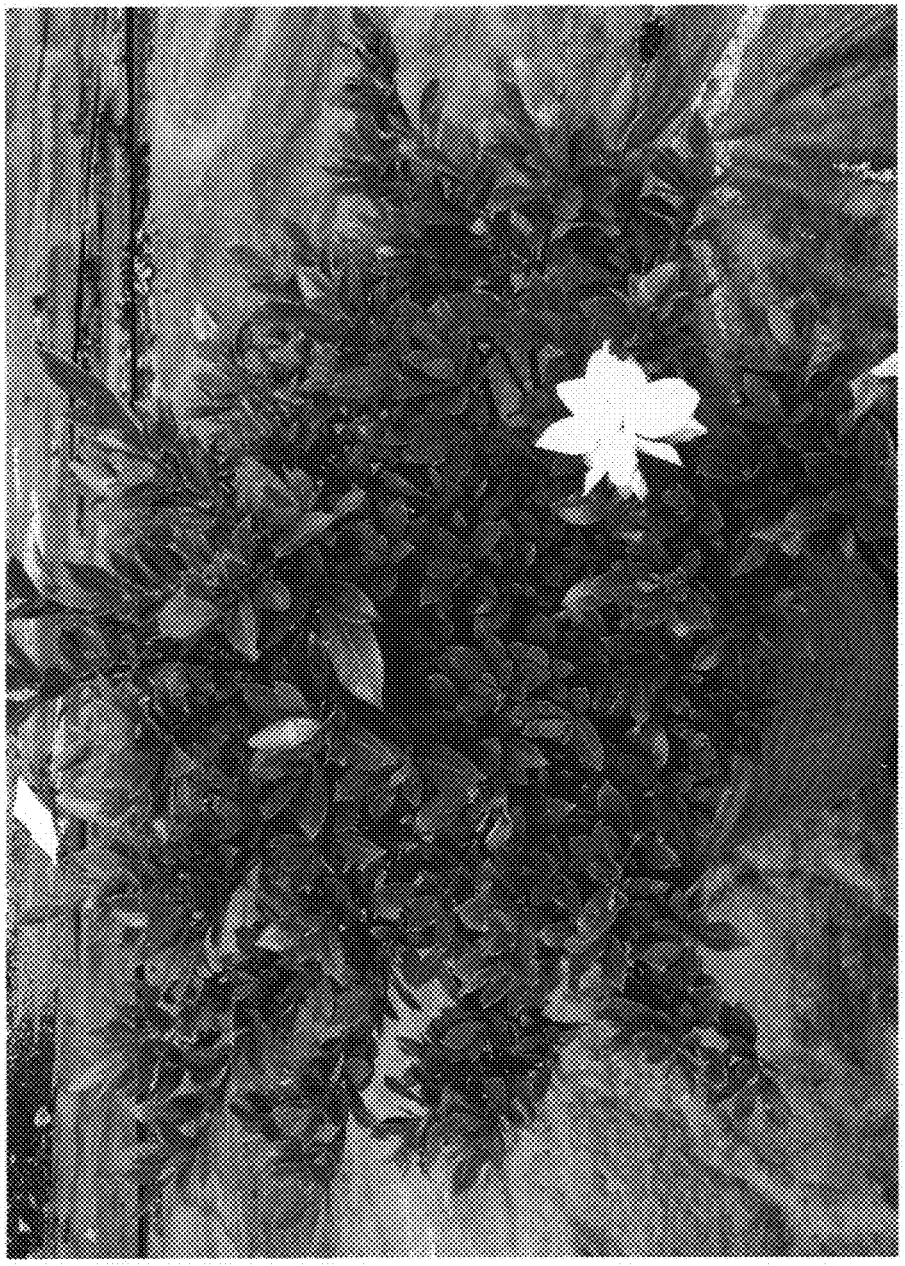

Latin name of the genus and species: *Gardenia augusta.* Variety denomination: 'PARWHI'.

BACKGROUND OF THE INVENTION

The new cultivar is a product of a planned breeding program by the inventor. The crossing was made in December 2012, at a nursery in Kulnura, Australia. The seed parent is the commercial variety *Gardenia* 'Buttons', U.S. Plant Pat. No. 24,229. The pollen parent is an unnamed, unpatented *Gardenia radicans*. The inventor discovered this new variety at the same nursery in March 2016.

After identifying the new variety as a potentially interesting selection, the inventor first organized propagation of 'PARWHI' by semi-hardwood vegetative cuttings during 2016 at the same commercial nursery in Kulnura, Australia. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'PARWHI' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PARWHI' These characteristics in combination distinguish 'PARWHI' as a new and distinct *Gardenia* cultivar:

1. Compact semi-erect habit.
2. Semi-double flower with many petals.

COMPARISON TO PARENT VARIETY

'PARWHI' is similar in most horticultural characteristics to the seed parent variety *Gardenia* 'Buttons'. Plants of the new cultivar 'PARWHI' however, differ in the following:

1. The new variety's habit is semi erect-spreading; parent's is erect.
2. The new variety has more petals than the parent variety.
3. Plant width of the new variety is broader than plant width of the seed parent.

'PARWHI' is similar in most horticultural characteristics to the pollen parent variety. Plants of the new cultivar 'PARWHI' however, differ in the following:

1. New variety has a medium leaf length; parent's is very short.
2. New variety has a medium leaf width; parent's is very narrow.

COMMERCIAL COMPARISON

'PARWHI' can be compared to the commercial variety *Gardenia hybrida* 'Ocean Pearl', unpatented. Plants of the new cultivar 'PARWHI' are similar to plants of 'Ocean Pearl' in most horticultural characteristics, however, plants of the new cultivar 'PARWHI' differ in the following:

1. New cultivar's flower diameter is medium; 'Ocean Pearl' has a small flower diameter.
2. New cultivar's plant width is medium; comparator is narrow.

'PARWHI' is similar in most horticultural characteristics to the commercial variety *Gardenia* 'LEEFOUR', U.S. Plant Pat. No. 27,600. Plants of the new cultivar 'PARWHI' however, differ in the following:

1. Flowers of the new variety are on average wider, having an average diameter of 6 to 9 cm, compared to the 5.5 to 7 cm diameter average of this comparator.
2. Petals of this comparator have a distinctive yellow flush not found on the completely white petals of the new variety.
3. Plants of the new variety have a broader, less erect form than plants of this comparator.

BRIEF DESCRIPTION OF THE PHOTOGRAPHS

The accompanying photograph in FIG. 1 illustrates in full color a plant of 'PARWHI' grown outdoors in Kulnura, Australia.

Figure 2:
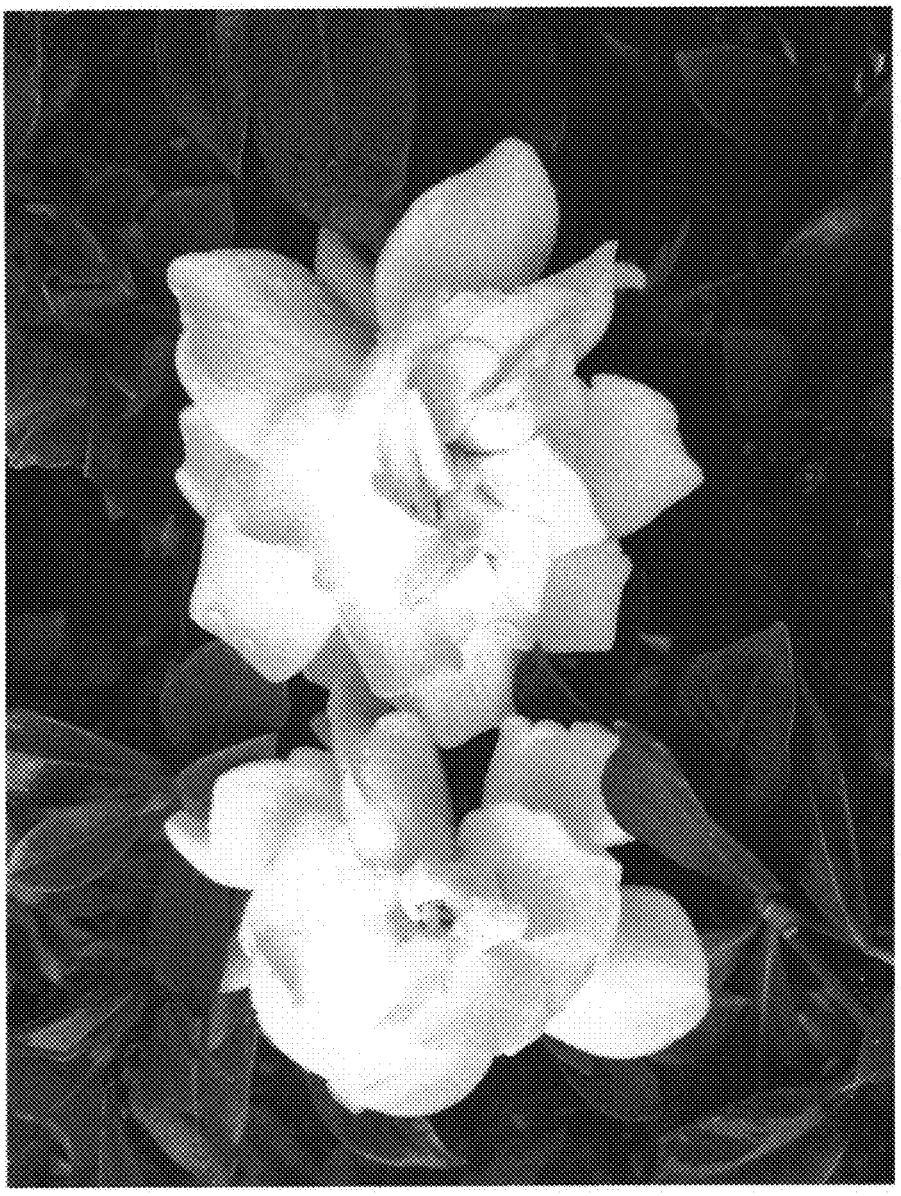

FIG. 2 shows a close up of a typical flower of the new variety. The plant is approximately 2 years old, and is shown in a 220 mm container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'PARWHI' plants grown outdoors in the Summer, in Kulnura, Australia. Plants are approximately 30 months old, in 300 mm pots. Measurements and numerical values represent averages of typical plant types.

Botanical classification: *Gardenia augusta* 'PARWHI'.

PROPAGATION

Typically by semi-hardwood cuttings in Spring and Summer.

Time to rooting: 30-50 days at approximately 22° C.

Time to produce a rooted plantlet: 100 days.

Root description: Fleshy, new roots colored RHS White 155D.

PLANT

Growth habit: Compact semi-erect evergreen shrub.

Height: 1 meter.

Plant spread: 1 meter.

Branching characteristics: Well branched.

Primary branches:

*Length*.—20-30 cm.

*Diameter*.—5-6 mm.

*Strength*.—Strong.

*Color*.—Dark brown. Near RHS Brown 200A.

*Texture*.—Rough.

Lateral branches:

*Color*.—Near RHS 144A.

*Length*.—Average range 7-12 cm.

*Diameter*.—Approximately 3-4 mm.

*Aspect*.—Semi-erect.

*Texture*.—Medium.

*Strength*.—Strong.

*Internode*.—Average range 30-40 mm.

Age of plant described: 800 days from a rooted cutting.

FOLIAGE

Leaf:

*Type*.—Simple.

*Arrangement*.—Whorled.

*Average length*.—8-9 cm.

*Average width*.—38 mm.

*Shape of blade*.—Elliptic, slightly obovate.

*Apex*.—Acuminate.

*Base*.—Attenuate.

*Attachment*.—Petiolate.

*Margin*.—Entire.

*Leaf internode*.—Average range 2-3 cm.

*Texture of top surface*.—Rippled.

*Texture of bottom surface*.—Rippled.

*Appearance of top surface*.—Medium glossy.

*Appearance of bottom surface*.—Dull.

*Color*.—Young foliage upper side: Near RHS 146A. Young foliage under side: Near RHS 146C. Mature foliage upper side: Near RHS 137A. Mature foliage under side: Near RHS 137D.

*Venation*.—Type: Pinnate. Venation color upper side: Near RHS 137A, midrib lighter. Venation color under side: Near RHS 150D, midrib lighter.

Petiole:

*Length*.—1 to 3 mm.

*Diameter*.—2 mm.

*Texture*.—Glabrous.

*Color*.—RHS Green 143C.

FLOWER

Bloom period: Spring-Summer.

Peduncle:

*Length*.—Average 10-15 mm.

*Diameter*.—Average 3-4 mm.

*Color*.—Near RHS 144B.

*Texture*.—Smooth.

*Aspect*.—Outward facing to upright.

*Strength*.—Strong.

Flowers:

Arrangement: Semi-double flowers arise from upper leaf axils.

*Height*.—Average 40-50 mm.

*Diameter*.—Average 60-90 mm.

*Facing direction*.—Outward facing to upright.

*Lastingness of individual flowers on plant*.—About 5 days.

*Persistent or self-cleaning*.—Mostly self-cleaning.

*Fragrance*.—Strong.

Tube:

*Tube length*.—Approximately 15 mm.

*Tube width a widest point*.—Approximately 10 mm.

*Tube width and narrowest point*.—Approximately 4-5 mm.

Petals:

*Unfused petal segments*.—Length: Approximately 30-45 mm. Width: Approximately 30-35 mm. Apex: Acute-rounded. Base: Fused at base into tube. Shape of petal: Obovate. Petal margin: Entire, with an occasional notch, frequently incurved or recurved.

*Petal arrangement*.—Rotate, overlapping.

*Petal number*.—About 16.

*Petal texture, upper and lower*.—Smooth.

*Color*.—Upper surface at first opening: Near RHS NN155C. Under surface at first opening: Near RHS NN155C. Inner surface at maturity: Near RHS 155C. Outer surface at maturity: Near RHS 155C. Upper surface at fading: Near RHS 155B. Under surface at fading: Near RHS 155B. Corolla Tube, Inner and Outer: RHS White N155C.

Bud:

*Shape*.—Elliptic-lanceolate.

*Length*.—5-6 cm.

*Diameter*.—1.5 cm.

*Color*.—Near RHS N144C.

Calyx/sepals:

*Quantity per flower*.—6-10.

*Arrangement*.—Whorled.

*Shape*.—Linear-lanceolate.

*Length*.—Average 25-30 mm.
*Width*.—Average 3-5 mm.
*Apex*.—Acuminate.
*Base*.—Broader than apex, fused to receptacle.
*Margin*.—Entire.
*Texture*.—Smooth.
*Color*.—Inner Surface: Near RHS 144B. Outer Surface: Near RHS 144B.

REPRODUCTIVE ORGANS

Stamens:
*Number*.—Average 6, often petaloid.
*Length*.—Approximately 10 mm.
*Width*.—Approximately 1 mm.
*Anthers*.—Length: Approximately 10 mm. Width: Approximately 1 mm. Color: Near RHS 153B. Pollen Quantity and Color: Scant. Yellow-green near RHS 153B. Shape: Linear.

Pistil:
*Number*.—1.
*Length*.—Approximately 10-20 mm.
*Style*.—Length: Approximately 10 mm. Color: Near RHS 158D. Stigma Shape and Color: Oval-orbicular, near RHS 155A. Ovary Shape, Size, Color: Approximately 10 mm in length, 5 mm in diameter, color near RHS 144C.

OTHER CHARACTERISTICS

Disease and pest resistance: Neither resistance nor susceptibility to the normal diseases and pests of *Gardenia* observed. Typical diseases of *Gardenia* include *Erysiphe polygoni*, and *Phomopsis gardenia*. Pests include the nematode *Meloidogyne* spp., white fly *Dialeurodes citri* and various scales, including *Ceroplastes japonicas, Icerya purchase, Fiorinia theae, Hemiberlesia rapax* and *Aspidiotus nerii*.

Temperature tolerance: 30° C. to 20° C. during the day. 15° C. to 20° C. during the night. No tolerance to drought.

Fruit/seed production: Not observed to date.

What is claimed is:

1. A new and distinct cultivar of *Gardenia* plant named 'PARWHI' as herein illustrated and described.

* * * * *